United States Patent [19]

Broida

[11] 4,406,659
[45] Sep. 27, 1983

[54] LEAKAGE-ABSORBING SUPPLEMENT TO UROSTOMY BAG

[76] Inventor: Marna J. Broida, 110 Dielman Rd., St. Louis, Mo. 63124

[21] Appl. No.: 320,349

[22] Filed: Nov. 12, 1981

[51] Int. Cl.³ ............................................. A61F 5/44
[52] U.S. Cl. ................................... 604/339; 604/342
[58] Field of Search ....... 128/295, 283, 284, DIG. 24, 128/DIG. 30, 760, 761, 762, 763; 229/56; 604/327, 332, 333, 334, 335–344

[56] References Cited

U.S. PATENT DOCUMENTS

| | | | |
|---|---|---|---|
| 2,423,060 | 6/1947 | Zaro | 128/283 |
| 2,595,934 | 5/1952 | Ginsburg | 128/283 |
| 3,528,423 | 9/1970 | Lee | 128/295 |
| 4,085,752 | 4/1978 | Canale | 128/283 |
| 4,172,066 | 10/1979 | Zweigle et al. | 128/284 |
| 4,256,110 | 3/1981 | Scoville | 604/343 |

Primary Examiner—Richard J. Apley
Assistant Examiner—J. L. Kruter
Attorney, Agent, or Firm—Jerome A. Gross

[57] ABSTRACT

A leakage-absorbing device to supplement a urostomy bag and absorb leakage across its seal flange, is readily put in place against the skin, inserted between the lower part of the flange and the bag; and is easily removed and replaced without removing the urostomy bag. It includes a pad whose lower portion is contained within a water-tight flexible pouch-like covering and whose upper yoke portion has a skin-facing side presented for absorption against the lower part of the base flange and the patient's skin. The device is supported by adhering to the skin immediately below the absorbent portion so presented.

10 Claims, 4 Drawing Figures

LEAKAGE-ABSORBING SUPPLEMENT TO UROSTOMY BAG

FIELD OF THE INVENTION

This invention deals with a device for urostomy patients to be worn supplemental to a urostomy bag, to absorb leakage across the adherent seal against the patient's skin.

BACKGROUND OF THE INVENTION

Urostomy operations involve removal of the bladder and provide the patient with a stoma, a small outlet (ordinarily made from the small intestine) which passes through the skin of the abdomen. To collect urine which drips more or less constantly from it, conventional urostomy bags are worn beneath the patient's clothing. These are relatively flat plastic bags which are adhered to the skin and may stay in place for several days, being emptied meanwhile through a valve at the tapered bottom of the bag. A typical urostomy bag has, for adhesion to the skin, a flexible base plate or flange with a central opening which fits about the stoma. Such flanges are somewhat rounded, ranging in extent from about 3½" to 5", to project inward from the adjacent wall of the bag.

During the post-operative period, patients are taught to use these bags, usually with increasing success. However, even an occasional event of leakage along the border between the adhered flange and the skin adds to the psychological damage already suffered by the urostomy patient. To even the brave and methodical patient, the problems of odor, leakage and skin irritation will require attention for the remainder of his life. For most patients the psychological impact is a restraint on normal physical, social and business activity, and even patients who learn to use urostomy bags with great success experience occasional failure.

To remove a urostomy bag adhered to the skin and replace it securely requires more time than a busy successful user may have available, a fact which may lead him into taking chances of leakage after the bag has been in place for several days. Hence even one who uses a urostomy bag successfully is faced from time to time by the prospect of its failure.

SUMMARY OF THE INVENTION

The purposes of the present invention include providing security in fact and peace of mind to urostomy patients by furnishing an effective device, supplemental to a urostomy bag, to absorb leakage along the border between the seal and the abdomen. A further purpose is to provide a supplemental device whose use is optional with the patient, of particular importance when he is learning to use the urostomy bag, as well as when even slight leakage would cause embarassment. Still another object is to provide a supplemental device which is inexpensive, which can be carried in the pocket or purse conveniently, applied quickly, and discarded readily.

Briefly summarizing the present invention, these purposes are met by providing, in special form and design, an absorbent pad whose materials are comparable to those used in sanitary pads which absorb the fluids of menstruation. On its entire outer side, the absorbent pad is faced with thin flexible light-weight plastic; a similar facing along the lower portion of the pad inner side is joined at its bottom and edges to the outer facing to form in effect a water-impermeable pouch. The pad extends upward in the shape of a yoke, fitted between the bag and the lower half of its adhesive flange. The upper edge of the inner plastic pouch wall is sufficiently below the upper yoke portion of the absorbent pad to bare a substantial area of the pad, which is thus presented against the wearer's skin and the lower edge of the flange. The upper edge of the inner pouch wall is itself adhered to the skin below this upward projecting area of absorbency, by a band of adhesive. This mounts and supports the supplemental device on the body of the wearer, as well as holding the yoke portion of the pad, unfaced on its inner side, in contact with the skin adjacent to and immediately below the flange seal.

The pouch may contain an ingredient which reacts with aqueous fluids such as urine to turn to semi-solid or gel. Such materials are conventional, and also serve to mask odors.

In a modified form of the present invention, an otherwise conventional urostomy bag is equipped with a supplemental inner wall which forms a pocket. Into it a replaceable pad is inserted, shaped to extend thereabove in a yoke about the lower part of the flange seal of the bag. This presents the upper portion of the pad in the space between the bag and its flange, against the lower edge of the flange and the skin of the wearer, in position to receive any leakage along the edge of the adhesive seal. The absorbent pad may be removed from the pocket of the urostomy bag and discarded, and a new pad inserted in the pocket at the time of such replacement. The upper edge of the pocket may be coated with a liquid adhesive and adhered to the patient's skin, to keep the pad in position.

DESCRIPTION OF THE PREFERRED EMBODIMENT

Figure 1:
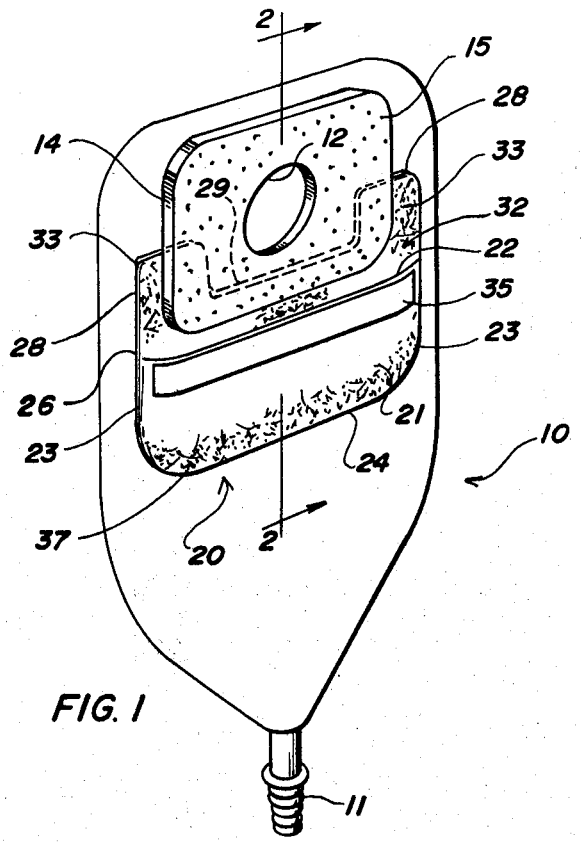
FIG. 1 is a view in perspective of a leakage-absorbing device to supplement a conventional urostomy bag.
Figure 2:
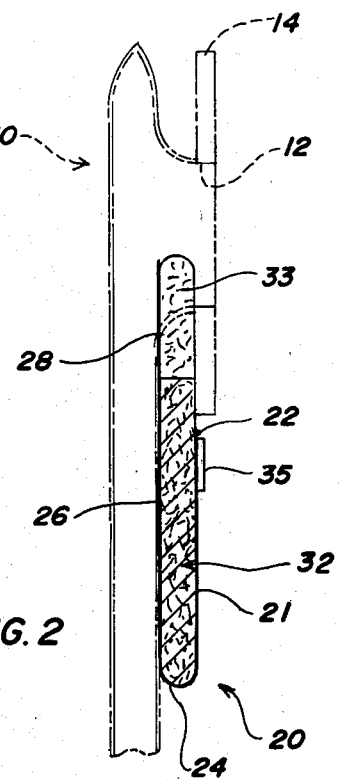
FIG. 2 is an enlarged cross-sectional view of the new device taken from FIG. 1, with portions of the urostomy bag shown in phantom lines.

A typical conventional urostomy bag not part of the present invention is generally designated 10 in FIGS. 1 and 2. It is a flat-sided bag having at its bottom a valve outlet 11, and having along the upper side of its inward-presented wall an inlet opening 12 to receive the stoma, the inlet opening 12 being surrounded by a large flexible base plate or flange 14 which extends spacedly from and generally parallel to the inner wall of the bag 10 inward. The inward surface of the flange 14 has an adhesive coating 15.

The preferred leakage-absorbing device of the present invention is for use under such a urostomy bag, that is, between the bag 10 and the skin of the patient, below the inlet opening 12. The upper portion of the device is thus interposed in the space between the bag and the flexible flange 14, to absorb such leakage as may occur across the flange edge.

The present device includes what is essentially a water impermeable pouch generally designated 20, comprising an inner wall 21 formed of thin flexible plastic material and having an upper edge 22, side edges 23, and a lower edge 24. The lower and side edges 24, 23 are joined to similar edge portions of an outer wall 26 to form the pouch 20. The outer wall 26 includes a yoke portion 28 extending above the inner wall upper edge 22; when the device is in place the outer arms of the yoke portion 28 rise approximately to the level of the center of the inlet opening 12 of the urostomy bag 10. The inward-cut bight 29 of the yoke portion 28 is essentially U-shaped, and should generally follow the conformation of the lower portion of the urostomy bag flange 14. As shown in FIGS. 1 and 2, the device is used with the bight 29 preferably fitted upward between the lower margin of the flange 14 and the bag 10.

Fitted in the pouch 20 so formed and extending above the upper edge 22 of the inner wall 21 is an absorbent pad generally designated 32 whose shape generally follows that of the pouch outer wall 26. Thus, an absorbent pad yoke portion 33 extends above the inner wall upper edge 22 as a facing for the inward-presented surface of the outer wall yoke portion 28, these parts being sealed together at their edges. In the preferred form of invention illustrated in FIGS. 1 and 2, the outer wall yoke portion 28 and the pad yoke portion 33 together extend a greater width above the upper edge 22 than the intended width of overlap by the flange 14. Specifically, such yoke extent is greater than half of the total depth of the bag flange 14, and the bight 29 is smaller than the flange outer edge.

A conventional adhesive strip 35 of the type having a removable paper cover lies as a band on the inward-presented margin of the upper edge 22 of the inner wall 21. In manufacture, prior to sealing the absorbent pad 32 in the pouch 20, particulate absorption flakes 37 are added, either within the pouch or by impregnation in the pad 32, to mask odors and also to convert liquid urine into a gel or semi-solid. Such particles 37 have previously been used in colostomy bags; typically they may be inert organic polymers which do not increase the fluid volume, but turn as much as 200 times the particle weight of trapped liquid into a semi-solid. Such flakes are conventionally sold in bulk under various trade styles, such as SPENCO Absorption Flakes.

In using the device of FIG. 1, with the urostomy bag 20 already adhered by its flange 14 to the skin of the wearer, the wearer removes the paper covering from the band of adhesive 35. With one hand the user bends the bag outward and raises the bag bottom upward. Holding the present device in his other hand, with its inner wall 21 presented toward the skin of the user, he presents the device between the flange 14 and the bag inner wall, so that the bight 29 of the device is immediately outward of and slightly above the lower edge of the flange 14 of the device, with the bight sides inward of the outer side edges of the flange 14. In this position, the exposed area of the pad 32 (adjacent to the bight 29 but above the inner wall upper edge 22) will be presented partly against substantially the entire lower half of the outer edge of said flange 14, and partly against the skin of the wearer. Once so positioned, he presses it against his skin, thus mounting the device in place on his body.

Leakage may occur across the adhesive 15 on the inner side of the flange 14 and will, as it drains downward, be absorbed into the yoke portion 33 of the pad 32, to drain gradually downward into the lower portion of the pouch 20, to be contained by the absorbency of the pad 32. Further, assuming that the flake particles 37 are contained in the pouch 20 or the pad 32 itself, they will transform the urine into a semi-solid or gel to avoid possible inadvertent squeezing out of the liquid in subsequent handling.

Should leakage occur, as is likely with patients first becoming accustomed to urostomy bags, and if the user cannot then conveniently remove and replace the bag, to restore the seal of the flange, the present supplement device is readily changed by drawing it away from the skin to destroy the adhesion of the strip 35. Then with the outlet end of the bag raised, the device is removed and a new one substituted, placed in the same manner. To avoid skin irritation from the leakage, this should be done only if the user cannot immediately replace the urostomy bag.

Figure 3:
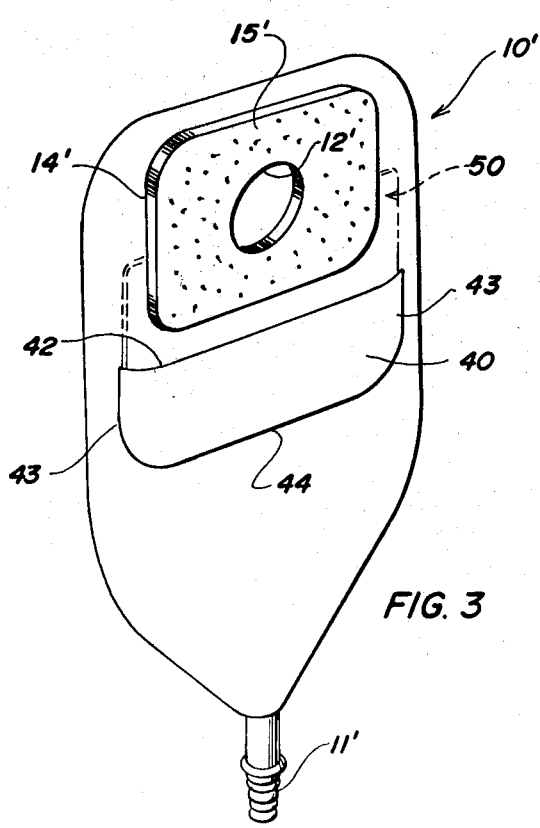
FIG. 3 is a modified form of the present invention, in which a supplemental pocket is added to a conventional urostomy bag for combination with the novel absorbent pad of FIG. 4, which in FIG. 3 is shown in phantom lines.
Figure 4:
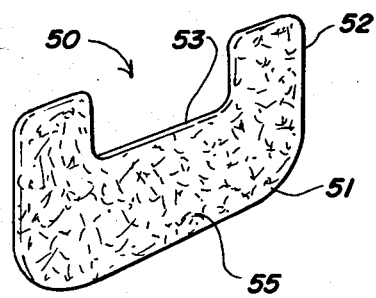
FIG. 4 is a perspective view of a novel absorbent pad for such combination with the urostomy bag of FIG. 3.

An alternate form of invention is shown in FIGS. 3 and 4. There a urostomy bag generally designated 10' has a similar bottom valve outlet 11', an inlet opening 12' and a base plate or flange 14' coated on its inner side with an adhesive 15'. To that extent, the bag 10' is conventional and not part of this invention.

In the present invention, however, a supplemental pocket generally designated 40 is added to the inward-presented surface of the bag 10' spacedly below the flange 14'. Specifically the pocket 40 has an upper edge 42, side edges 43 and bottom edge 44, the side and bottom edges being adhered, as by heat sealing, to the inward-presented wall of the bag 40 while the pocket upper edge 42 is free therefrom. It is so spaced below the lower edge of the flange 14' as to permit exposure therebetween of a substantial width of the upper portion of a replaceable absorbent pad generally designated 50.

The replaceable pad 50 is substantially the same size as the pad 32 of the embodiment of FIGS. 1 and 2, to absorb leakage along the same portion of the flange seal. Thus, the pad 50 has a lower portion 51 which fits within the pocket 40 and an upper yoke portion 52 which extends above the pocket upper edge 42 and has a bight 53 which fits between the bag flange 14' and its inward wall.

In using this modification of the invention with the pocket-equipped urostomy bag 10' attached by its flange 14' to the user's abdomen, the user grasps the lower portion of the bag 10 and bends the bag upward and outward, so as to make available the opening of the pocket 40 above the pocket upper edge 42. He inserts a pad therein, and manipulates its upper yoke portion 52 to fit beneath and along the outer edge of the flange 14'. He also applies an adhesive along the margin of the pocket edge 42, and presses that margin against the skin. For this purpose, a medical-grade silicone with low potential for skin irritation is preferred, such as HOLLISTER Medical Adhesive. The replaceable pad 50, although itself free of adhesion to any plastic, is thus positioned so that leakage across the surface of the flange 14 will be absorbed in the same manner as by the device shown in FIG. 1.

Preferably the replaceable pad 50 is impregnated with gel-forming particles 55 in the same manner as heretofore described.

Whether using such replaceable pads 50 of FIG. 4 in the pocket 40 of a modified urostomy bag shown in FIG. 3, or in using the preferred device of FIG. 1, the added confidence of and convenience to the user are great. For example, either the device of FIG. 1 or the replaceable pads 50 of FIG. 4 are readily carried in the pocket or purse of the user, and may be utilized without removing a urostomy bag from its adhered position on the abdomen of the wearer. The invention thus serves not only during the initial period of training, but thereafter whenever the extra security of the device or pad may be desired.

From this description variations will occur to those familiar with the art.

For example, the outer wall yoke portion 28 and pad yoke portion 33 may rise to a greater or lesser extent, with the cut-out or bight 29 proportioned to fit adjacent to at least the lowermost portions of the bag flange 14 and some substantial portions of the flange thereabove, to receive leakage across the border between the flange seal and the skin when the wearer's body is upright.

I claim:

1. For wear under a urostomy bag of the type having a skin-adhered flange to be sealed surrounding the stoma,
   a replaceable pad-like device for absorbing leakage between such flange and the skin, comprising:
   (a) a water-impermeable pouch wider than such flange and having
   an inner wall formed of thin flexible plastic material and having an upper edge spacedly below such flange, and
   an outer wall formed of similar material and including a yoke portion extending upward above the upper edge of the inner wall, said upward-extending portion having a cut-out so proportioned as to fit adjacent to at least the lowermost portion of such flange and a substantial flange portion thereabove, whereby to receive leakage across the border between the seal and the skin when the wearer's body is upright, in combination with
   (b) an absorbent pad both within the pouch and extending above said upper edge of the inner wall substantially co-extensive with and covering that surface of said upward-extending yoke portion of the outer wall of the pouch which is presented toward the wearer's body, together with
   (c) means to mount said device to the body of the wearer with said covered yoke portion fitted adjacent to the outer edge of substantially the lower half of such flange.

2. A leakage-absorbing device as defined in claim 1, wherein the means to mount to the body of the wearer comprises
   a band of adhesive extending across the device adjacent to said upper portion of the outer edge of the inner wall of the pouch.

3. A leakage-absorbing device as defined in claim 1, wherein the portion of said absorbent pad so covering said upward-extending portion of the outer pouch wall is sealed thereto.

4. A leakage-absorbing device as defined in claim 1, wherein the contents of said pouch include
   material of the type which, on being contacted by urine, forms a semi-solid or gel.

5. A leakage-absorbing device as defined in claim 1, wherein gel-forming matter is incorporated in said pad.

6. For wear under a urostomy bag of the type having a skin-adhered flange to be sealed surrounding the stoma,
   a replaceable pad-like device comprising:
   an inner flexible water-impermeable plastic member means wider than such flange and having an upper edge spacedly below such flange,
   an absorbent pad affixed outwardly thereof, the pad having, above the upper edge of said inner member, a yoke portion whose width substantially corresponds with that of said inner member means and whose height extends beyond the lower edge of such flange, and
   an outer member formed of similar plastic material, the bottom and lower side edges of the inner member being impermeably joined to the outer member, whereby to form a liquid-retaining pouch,
   said outer member having a yoke portion substantially co-extensive with the yoke portion of the absorbent pad,
   the bight of said yoke portions being so sized as to fit adjacent to the lower edge of such flange and the skin therebeneath,
   whereby urine escaping along such seal edge is absorbed into the pad and carried downward into the pouch portion of said device.

7. A device as defined in claim 6, wherein
   the contents of said pouch include material of the type which, on contact with urine, forms a semi-solid or gel.

8. A device as defined in claim 6, wherein
   the extent of said yoke portions above the upper edge of the inner member exceeds one-half of the depth of such flange seal, and
   the bights of said yoke portions are smaller than the outer edge of the lower portion of the flange seal,
   whereby to present a pad area of absorbency against such edge of the flange seal and the skin therebeneath.

9. In a urostomy bag of the flat-sided type having an outer wall joined about its edges to those of an inner wall presented inward toward the wearer, said inward presented wall having an inlet opening surrounded by a flexible flange adapted to be adhered to the skin of the wearer and having a lower flange edge, the improvement comprising
   a supplemental pocket formed of a thickness of flexible impermeable material positioned on and having side edges and a bottom edge adhered to said inner bag wall spacedly beneath the flange seal and there having a pocket upper edge free from said inner bag wall, the width of said pocket being substantially greater than the width of said flange, in combination with
   a replaceable leakage-absorbing pad fitting into the pocket and whose width is substantially co-extensive with said pocket, said pad having a yoke portion extending above the pocket upper edge sufficiently to bear against substantially the entire lower half of the outer edge of said flange.

10. The improvement as defined in claim 9, in which
    the leakage-absorbing pad includes material of the type which, on contact with urine forms a semi-solid or gel.

* * * * *